(12) United States Patent
Nakayama et al.

(10) Patent No.: US 8,895,963 B2
(45) Date of Patent: Nov. 25, 2014

(54) ORGANIC SEMICONDUCTOR MATERIAL, ORGANIC SEMICONDUCTOR THIN FILM, AND ORGANIC THIN-FILM TRANSISTOR

(75) Inventors: Ken-ichi Nakayama, Yonezawa (JP); Junji Kido, Yonezawa (JP); Yong-Jin Pu, Yonezawa (JP); Yohei Hashimoto, Yonezawa (JP); Naomi Oguma, Chuo-ku (JP); Naoki Hirata, Chuo-ku (JP)

(73) Assignees: Dainichiseika Color & Chemicals Mfg. Co., Ltd., Tokyo (JP); Ken-ichi Nakayama, Yonezawa-shi, Yamagata (JP)

( * ) Notice: Subject to any disclaimer, the term of this patent is extended or adjusted under 35 U.S.C. 154(b) by 468 days.

(21) Appl. No.: 13/138,976

(22) PCT Filed: May 11, 2010

(86) PCT No.: PCT/JP2010/058255
§ 371 (c)(1),
(2), (4) Date: Nov. 8, 2011

(87) PCT Pub. No.: WO2010/131764
PCT Pub. Date: Nov. 18, 2010

(65) Prior Publication Data
US 2012/0056166 A1    Mar. 8, 2012

(30) Foreign Application Priority Data
May 11, 2009  (JP) .................................. 2009-114620

(51) Int. Cl.
  *H01L 51/54* (2006.01)
  *C07D 409/14* (2006.01)
  *H01L 51/00* (2006.01)
  *C07D 495/04* (2006.01)
  *C07D 495/14* (2006.01)
  *C07D 209/48* (2006.01)

(52) U.S. Cl.
  CPC .......... *C07D 209/48* (2013.01); *H01L 51/0074* (2013.01); *H01L 51/0068* (2013.01); *C07D 409/14* (2013.01); *C07D 495/04* (2013.01); *C07D 495/14* (2013.01); *H01L 51/0053* (2013.01)
  USPC .............. 257/40; 257/E51.024; 257/E51.005; 548/461

(58) Field of Classification Search
  None
  See application file for complete search history.

(56) References Cited

U.S. PATENT DOCUMENTS 6,068,792 A  5/2000  Watabe
8,378,336 B2  2/2013  Kitamura

FOREIGN PATENT DOCUMENTS

| JP | 50030875 A | * | 3/1975 |
|---|---|---|---|
| JP | 2004-82438 A | | 3/2004 |
| JP | 2006-60169 A | | 3/2006 |
| JP | 2006-206503 A | | 8/2006 |
| JP | 2008-513544 A | | 5/2008 |
| JP | 2010-3831 A | | 1/2010 |
| WO | WO 2007/050049 A1 | | 5/2007 |

OTHER PUBLICATIONS

Sato et al. Polymer Journal 2002, 34, 601-607. Year of publication: 2002.*
English translation of JP50-030875. Date of publication: Mar. 27, 1975.*
Chesterfield, Rj., et al., "Organic Thin Film Transistors Based on N-Alkyl Perylene Diimides: Charge Transport Kinetics as a Function of Gate Voltage and Temperature," Journal of Physical Chemistry B, vol. 28 (2004), pp. 19281-19292.
Kobayashi, S., et al., "Fabrication and Characterization of C60 Thin-Film Transistors with High Field-Effect Mobility," Applied Physics Letters, vol. 82, No. 25 (Jun. 23, 2003), pp. 4581-4583.
Sato, M., et al., "Preparation, Thermotropic Liquid-Crystalline and Fluorescent Properties of Semi-Rigid Homo- and Copoly(ester-imide)s Composed of . . . ," Polymer Journal, vol. 34, No. 8 (2002), pp. 601-607.
Tatemich, S., "High Mobility n-Type Thin-Film Transistors Based on N,N'-Ditridecyl Perylene Diimide with Thermal Treatments," Applied Physics Letters, vol. 89 (2006), pp. 112108.
Waldauf, C., et al., "Solution-Processed Organic n-Type Thin-Film," Advanced Materials, vol. 15, No. 24 (Dec. 17, 2003), pp. 2084-2088.
European Patent Office, Extended European Search Report for European Patent Application No. EP 10 77 5020, Sep. 24, 2012, Rijswijk, Netherlands.
Japan Patent Office, Office Action for Japan Patent Application No. 2011-534958, May 7, 2013, Tokyo, Japan.

* cited by examiner

*Primary Examiner* — Andrew K Bohaty
(74) *Attorney, Agent, or Firm* — Taft Stettinius & Hollister LLP

(57) ABSTRACT

An organic semiconductor material is represented by the following formula (F):
wherein A represents a cyclic conjugated skeleton structure formed of one or more aromatic rings, and $R_1$ and $R_2$ each independently represent a substituted or unsubstituted alkyl group. The organic semiconductor material has high electron mobility and high on/off ratio, and can form an organic semiconductor thin film by a solution process making use of its solution.

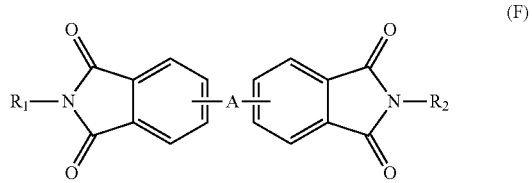

(F)

18 Claims, 2 Drawing Sheets

ORGANIC SEMICONDUCTOR MATERIAL, ORGANIC SEMICONDUCTOR THIN FILM, AND ORGANIC THIN-FILM TRANSISTOR

TECHNICAL FIELD

This invention relates to an organic semiconductor material which is a phthalimide compound having alkylated phthalimido groups at both ends of a cyclic conjugated skeleton structure formed of one or more aromatic rings, an organic semiconductor thin film comprising the material, and an organic thin-film transistor which makes use of the organic semiconductor thin film and exhibits n-type characteristics.

BACKGROUND ART

The progress of a high-level information-oriented society in recent years is remarkable, and the development of digital technologies has led to the penetration of computers and communication technologies such as computer networks in everyday life. Keeping in step with this penetration, flat-screen TV sets and notebook-size personal computers have become increasingly popular, resulting in an increasing demand for displays such as liquid crystal displays, organic EL displays and electronic paper displays. Especially in recent years, there is an outstanding move toward larger displays of higher definition, and therefore, it is required to assemble an ever increasing large number of field-effect transistors corresponding to the number of pixels. In a liquid crystal display, the liquid crystal can be driven by providing the respective pixels with field-effect transistors as active elements and performing on/off control of signals.

As field-effect transistors for use as active elements, thin-film transistors can be used. The performance of a thin-film transistor is determined by its semiconductor material and configuration. In particular, the availability of high carrier mobility and high on/off ratio makes it possible to obtain a large current, thereby not only enabling to drive an organic EL device or the like but also enabling to miniaturize the thin-film transistor and to provide an improved contrast.

For thin-film transistors useful as active elements, a silicon-based semiconductor material such as amorphous silicon or polysilicon can be used. A thin-film transistor is fabricated by forming such a silicon-based semiconductor material in a multilayered structure such that source, drain and gate electrodes are successively formed on a substrate.

For the fabrication of thin-film transistors making use of a silicon-based semiconductor material, large-scale and costly fabrication facilities are needed, and because of the use of photolithography, many process steps have to be gone through, resulting in high fabrication cost. Furthermore, the fabrication requires high temperatures of from 300° C. to 500° C. or even higher, which lead not only to still higher fabrication cost but also to difficulty in forming thin-film transistors on plastic substrates or plastic films.

Organic thin-film transistors, which make use of organic semiconductor thin films made of an organic semiconductor material, are fabricated by a vapor deposition process or a solution process, and have the possibility of lower cost, larger area and lighter weight. Further, organic semiconductor layers can be formed at a lower temperature compared with inorganic semiconductor layers, can realize cost reduction and can be formed on plastic substrates or plastic films, and therefore, can be applied to lightweight and flexible, electronic devices or the like.

Many organic semiconductor materials have been studied to date, and those making use of conjugated high-molecular compounds or low-molecular compounds as organic semiconductor layers are known. Semiconductor materials include n-type semiconductor materials and p-type semiconductor materials. In an n-type semiconductor material, electrons move as main carriers to produce an electric current. In a p-type semiconductor material, on the other hand, holes move as main carriers to produce an electric current.

As organic semiconductor materials that exhibit high performance as organic thin-film transistors, pentacene materials and thiophene materials are known. These materials are semiconductor materials that exhibit p-type characteristics. However, reports on n-type organic semiconductor materials of high performance are limited. There is, accordingly, an outstanding desire for n-type organic semiconductor materials of high performance. For further developments of organic electronics, lower power consumption, simpler circuits and the like are essential, and organic complementary MOS circuits which both n-type and p-type organic semiconductor materials require, such as complementary metal-oxide semiconductors (CMOS), are needed.

As n-type organic semiconductor materials, naphthalene imide, naphthalene diimide, and derivatives thereof are known to date. However, none of these organic semiconductor materials have been reported to have high performance as thin-film transistors. Further, potential utility of low-molecular compounds having the perylene skeleton inorganic thin-film transistors capable of exhibiting high performance is described (NPL 1: 0.6 $cm^2$/Vs electron mobility)(NPL 2: 2.1 $cm^2$/Vs electron mobility). However, these materials have large aromatic rings, respectively. Therefore, they have substantially no solubility in solvents, thereby making it difficult to fabricate thin-film transistors by a solution process.

Further, organic thin-film transistors making use of fullerene (C60) are known to exhibit n-type characteristics. Fabrication of a thin-film transistor making use of a vapor-deposited thin film of fullerene has been reported (NPL 3: 0.56 $cm^2$/Vs electron mobility).

Also reported are thin-film transistors with organic semiconductor thin films, each of which make use of a fullerene derivative solubilized by introducing a substituent group into a fullerene and has been formed by a solution process. For example, a thin-film transistor making use of a fullerene with phenyl C61-butyric acid methyl ester introduced therein as an organic semiconductor layer is reported to have an electron mobility of 0.0035 $cm^2$/Vs (NPL 4), and in the case of a C60 derivative with a long-chain alkyl group introduced therein, specifically C60-fused N-methylpyrrolidine-meta-C12 phenyl, an electron mobility of 0.067 $cm^2$/Vs has been reported (PTL 1).

However, organic thin-film transistors fabricated by using fullerene or fullerene derivatives as organic semiconductor materials have a drawback in that fullerene is a costly material, organic semiconductor materials as its derivatives are also expensive, and therefore, economical devices can be hardly fabricated.

In addition, the possibility of formation of a film with a π-electron compound, which has a skeleton structure containing a π-electron ring and has perfluoroalkylphenyl groups at both ends of the skeleton, as an n-type organic semiconductor material by a solution process, a printing process such as inkjet printing or a vapor deposition process is described. A description is made about the fabrication of an organic thin-film transistor by a solution process, but no description is made of a fabrication example of an organic thin-film transistor by a solution process (PTL 2).

Also described are organic thin-film transistors fabricated by using, as n-type semiconductor materials, compounds having carbonyl groups at ends of oligothiophenes. In each of these compounds, however, the carbonyl groups are directly bound to the oligothiophene. To obtain stable performance, four or more thiophene rings have to be coupled together so that high solubility is hardly obtainable. Their use in a solution process, therefore, requires to employ precursors, leading to a problem that a step such as acid treatment is needed (PTL 3).

As has been described above, no n-type organic semiconductor material has been found yet to be economical, to have solubility in a solvent, and hence, to permit the formation of an organic thin film by a solution process. Further, no report has been made on an organic semiconductor thin film or organic thin-film transistor having high electron mobility and high on/off ratio.

CITATION LIST

Patent Literature

PTL 1: JP-A-2006-060169
PTL 2: JP-A-2006-206503
PTL 3: JP-A-2008-513544

Non Patent Literature

NPL 1: Reid J. Chesterfield et al., J. Phys. Chem. B., 108(50), 19281 (2004)
NPL 2: M. Ichikawa et al., Appl. Phys. Lett., 89(11), 112108 (2006)
NPL 3: S. Kobayashi et al., Appl. Phys. Lett., 82(25), 4581-4583 (2003)
NPL 4: C. Waldauf et al., Advanced Materials, 24(15), 2084-2088 (2003)

SUMMARY OF INVENTION

Technical Problem

Therefore, an object of the present invention is to provide an organic semiconductor material, which has high electron mobility and high on/off ratio and permits the formation of an organic semiconductor thin film by a solution process that makes use of its solution. Another object of the present invention is to provide an organic thin-film transistor that is fabricated by using the organic semiconductor material.

Solution to Problem

The above-described objects can be achieved by the present invention to be described hereinafter. Described specifically, the present invention provides an organic semiconductor material represented by the following formula (F):

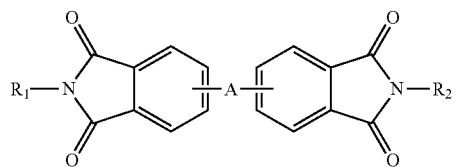

wherein A represents a cyclic conjugated skeleton structure formed of one or more aromatic rings, and $R_1$ and $R_2$ each independently represent a substituted or unsubstituted alkyl group.

In the above-described organic semiconductor material, it may be preferred that $R_1$ and $R_2$ each independently represent a linear or branched, $C_{1-18}$ alkyl group; $R_1$ and $R_2$ each independently represent a linear or branched, $C_{1-18}$ alkyl group hydrogen atoms of which have been partly substituted by a like number of fluorine atoms; A is a benzene ring, naphthalene ring, anthracene ring, phenanthrene ring, pyrene ring, triphenylene ring, naphthacene ring, pentacene ring, biphenyl ring, thiophene ring, bithiophene ring, terthiophene ring, quaterthiophene ring, quinquethiophene ring, sexithiophene ring, septithiophene ring, octithiophene ring, benzothiophene ring, thienothiophene ring, or dithienothiophene ring; A contains one or more fluorine atoms, bromine atoms, chlorine atoms or cyano groups as substituents; or A comprises preferably from 1 to 6 aromatic rings, more preferably from 1 to 4 aromatic rings.

In the above-described organic semiconductor material, it may also be preferred that A has one of the following structures (1) to (7).

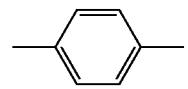
(1)

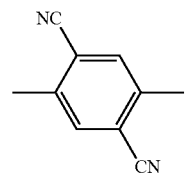
(2)

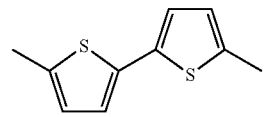
(3)

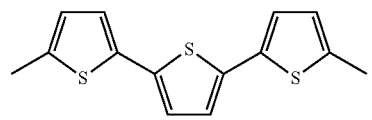
(4)

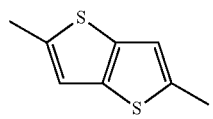
(5)

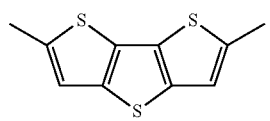
(6)

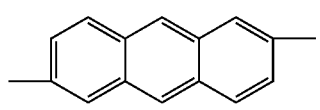
(7)

The present invention also provides an organic semiconductor thin film comprising the above-described organic semiconductor material according to the present invention; and an n-type organic thin-film transistor formed on a substrate and having a gate electrode, gate insulating layer, organic semiconductor layer, source electrode and drain electrode, wherein the organic semiconductor layer comprises the above-described organic semiconductor thin film according to the present invention. This organic thin-film transistor may have an electron mobility of preferably from 0.001 to 5.0 cm²/Vs, more preferably from 0.01 to 5.0 cm²/Vs.

Advantageous Effects of Invention

According to the present invention, an organic semiconductor material can be provided, which has high electron mobility and high on/off ratio and permits the formation of an organic semiconductor thin film by a solution process that makes use of its solution. It is also possible to provide an organic thin-film transistor that is fabricated by using the organic semiconductor material.

DESCRIPTION OF EMBODIMENTS

Figure 1:
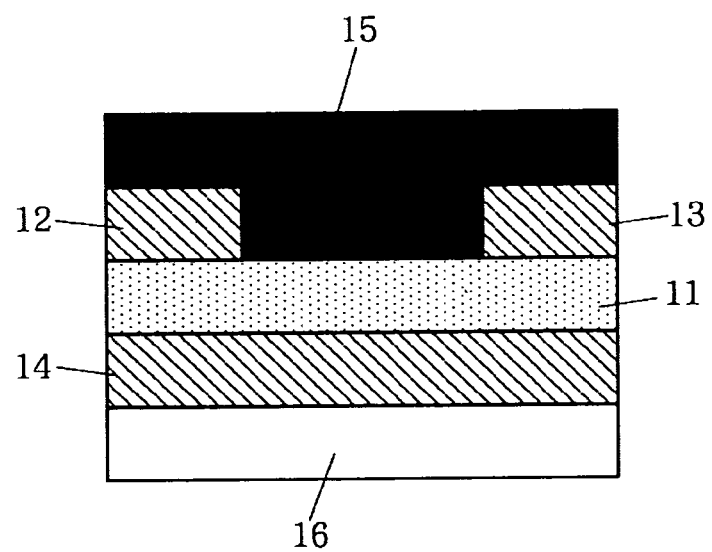
FIG. 1 is a cross-sectional view illustrating one embodiment of the configuration of the organic thin-film transistor according to the present invention.

The embodiments of the present invention will hereinafter be described in detail. It is, however, to be noted that the present invention is not limited to or by the following embodiments and can be practiced within a scope not departing from the gist of the present invention. A description will first be made about the organic semiconductor material of the present invention represented by the formula (F).

The organic semiconductor material of the present invention represented by the formula (F) has phthalimido groups at both ends thereof. Each phthalimido group contains at an end thereof two carbonyl groups in each of which an oxygen atom is bonded to a corresponding carbon atom via a double bond. The organic semiconductor material of the present invention represented by the formula (F) is provided with strong electron drawing property owing to these carbonyl groups, and therefore, can serve as an organic semiconductor material that shows n-type characteristics. As the organic semiconductor material of the present invention represented by the formula (F) contains two carbonyl groups at each end thereof, it has a deep HOMO level, and therefore, has the possibility of providing an organic thin-film transistor that can exhibit stable performance despite the existence of impurities such as oxygen and water contained in the atmosphere.

Owing to interaction between molecules of the cyclic conjugated skeleton structure formed of one or more aromatic rings in the compound of the present invention represented by the formula (F), the compound can exhibit characteristics as an n-type semiconductor material. The cyclic conjugated skeleton structure (hereinafter called "the skeleton structure A") formed of one or more aromatic rings can form strong stacking and can achieve high electron mobility in an organic semiconductor thin film formed by a vapor deposition process or solution process.

Any skeleton structure can be used as the skeleton structure A in the present invention insofar as it is a residual group of a cyclic conjugated compound formed of one or more aromatic rings. Examples of the skeleton structure A include skeleton structures formed of one or more six-membered rings, such as benzene ring, naphthalene ring, anthracene ring, phenanthrolene ring, pyrene ring, triphenylene ring, naphthacene ring, pentacene ring and biphenyl ring; and π-electron system structures containing one or more sulfur-containing heterocyclic rings, such as thiophene ring, bithiophene ring, terthiophene ring, quaterthiophene ring, quinquethiophene ring, sexithiophene ring, septithiophene ring, octithiophene ring, benzothiophene ring, thienothiophene ring and dithienothiophene ring.

Although not specifically limited, the number of aromatic ring(s) contained in a π-electron system compound, which serves as the skeleton structure A, may preferably be from 1 to 6. For obtaining high solubility, however, particularly preferred is from 1 to 4. The compound, which has alkylated phthalimido groups at both ends of the π-electron system compound as the skeleton structure A in the present invention, contains the phthalimido groups at both ends thereof, and therefore, can realize high electron mobility and high on/off ratio although the number of the aromatic ring(s) as a core is 1 or more, preferably from 1 to 6, particularly preferably from 1 to 4.

As this skeleton structure A, a heterocyclic compound can also be used. As a particularly preferred heterocyclic compound, a heterocyclic compound having a thiophenyl-containing skeleton structure can be mentioned. Skeleton structures formed of one or more heterocyclic rings as aromatic rings include the following structures.

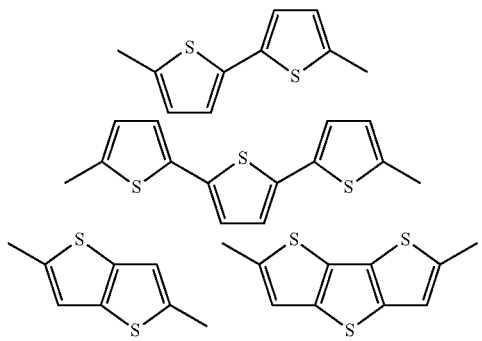

These skeleton structures may be substituted by one or more, preferably plural halogen atoms such as fluorine atoms, chlorine atoms, bromine atoms or iodine atoms, cyano groups, nitro groups or the like, desirably at symmetrical positions to provide the corresponding compounds of the formula (F) with improved solubility in solvents and also to realize stable transistor characteristics in the atmosphere.

Such substituted skeleton structures include, but are not specifically limited to, the following skeleton structures, which are residual groups of chlorinated, brominated and cyanated π-electron system cyclic compounds.

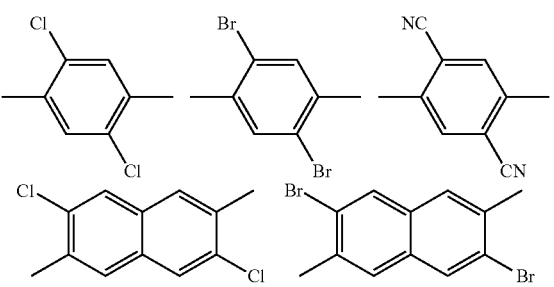

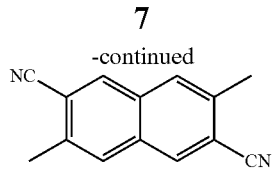

In the formula (F), the alkyl group represented by $R_1$ and $R_2$ enables the dissolution of the compound represented by the formula (F) in a solvent, and therefore, enables the formation of an organic semiconductor thin film by a solution process. No particular limitation is imposed on $R_1$ and $R_2$ insofar as the above-described definition is met. Specific examples include $C_1$-$C_{18}$ linear alkyl groups such as methyl group, ethyl group, propyl group, butyl group, pentyl group, hexyl group, heptyl group, octyl group, nonyl group, decyl group, undecyl group and dodecyl group, preferably $C_1$-$C_{12}$ linear alkyl groups, more preferably $C_3$-$C_{10}$ linear alkyl group, still more preferably $C_8$-$C_{10}$ linear alkyl groups, even still more preferably $C_8$ linear alkyl group. Further, the introduction of branched alkyl groups provides the compound represented by the formula (F) with increased solubility, and therefore, makes it possible to perform solution deposition with a high-concentration solution.

The use of fluorine-substituted alkyl groups as $R_1$ and $R_2$ in the formula (F) makes it possible to prevent impurities such as water, oxygen and air from penetrating into an organic semiconductor thin film, and therefore, to exhibit stable n-type semiconductor characteristics.

Examples of the skeleton structure of the compound of the present invention represented by the formula (F) include structures represented by the following formulas (I) to (V):

(I)

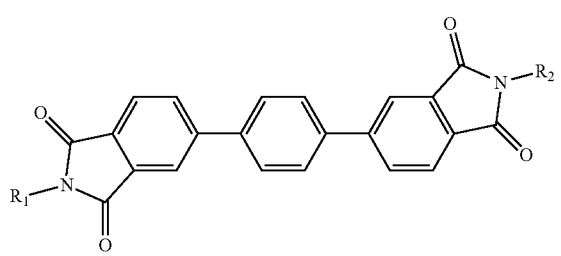

(II)

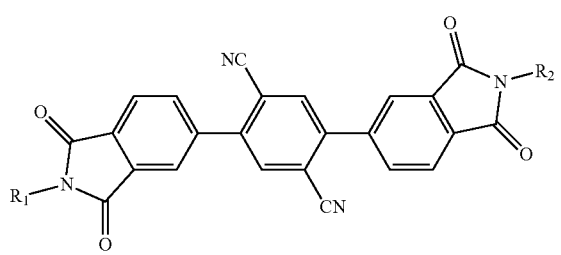

(III)

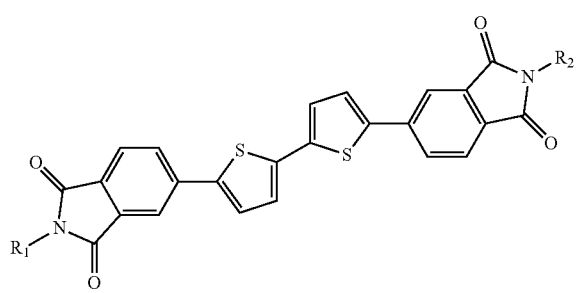

(IV)

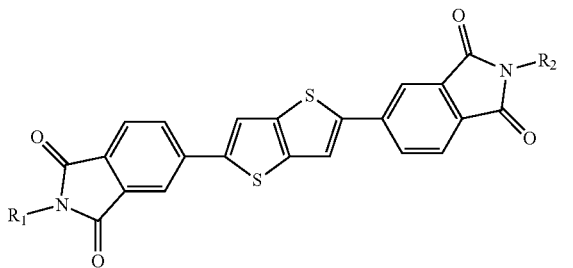

(V)

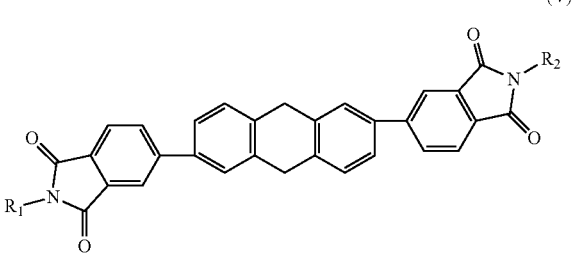

wherein $R_1$ and $R_2$ are as defined above (specifically, octyl groups).

For the synthesis of the compound of the present invention represented by the formula (F), any process can be practiced without any particular limitation insofar as it can introduce alkylated phthalimido groups to both ends of the skeleton structure A. Although not specifically limited, such a process can be, for example, the Suzuki-Miyaura coupling reaction. By coupling a halogenated compound of the skeleton structure A and a boron-containing alkylphthalimide compound together by the Suzuki-Miyaura coupling reaction, it is possible to synthesize a compound having alkylated phthalimide derivative groups at both ends of the skeleton structure A formed of the π-electron system cyclic structure. As an alternative, a boron compound of the skeleton structure A and a halogenated alkylphthalimide can be coupled together by the Suzuki-Miyaura coupling reaction. The Suzuki-Miyaura coupling reaction can be carried out, for example, by a reaction at a temperature of from room temperature to 125° C. or so for from 12 to 48 hours in a solvent under the action of a palladium catalyst and a nucleophilic species such as a base.

The reaction solvent can be, but is not specifically limited to, tetrahydrofuran, N,N-dimethylformamide, dimethylsulfoxide, toluene, or the like. As an alkali metal base, sodium carbonate, potassium carbonate, sodium hydroxide, potassium hydroxide, potassium carbonate or the like can be used. The palladium catalyst can be tetrakis(triphenylphosphine) palladium [Pd(PPh$_3$)$_4$], palladium acetate, or the like.

For use in an organic thin-film transistor, it is preferred to use the compound of the formula (F) in a form of increased purity. A decrease of impurities leads to a decrease of causes that prevent movement of electrons in an organic semiconductor thin film, thereby increasing the mobility of electrons in an organic thin-film transistor and providing the transistor with improved performance. As a method for increasing the purity, purification methods such as preparative chromatography, recrystallization and sublimation purification can be used either singly or in combination to use the compound of the formula (F) in a form of increased purity.

The above-mentioned compound of the present invention represented by the formula (F) exhibits characteristics as an n-type organic semiconductor material, and the use of the compound of the present invention as an organic semiconductor thin film makes it possible to fabricate an organic thin-film transistor.

A more detailed description will hereinafter be made about organic thin-film transistors according to the present invention. It should, however, be borne in mind that the present invention is not limited to their configurations.

In an organic thin-film transistor, the MIS structure (Metal-Insulator-Semiconductor structure) that a gate electrode is insulated by an insulating film is often used in general. An organic thin-film transistor to which the present invention can be applied has an organic semiconductor layer formed of an organic semiconductor thin film, and is composed of a source electrode, a drain electrode, and also, a gate electrode and a gate insulating layer. In the organic thin-film transistor according to the present invention, the organic semiconductor layer is made of the organic semiconductor material which is the compound (the compound represented by the formula (F)) having the alkylated phthalimido groups at both ends of the skeleton structure formed of the π-electron system cyclic structure.

Figure 2:
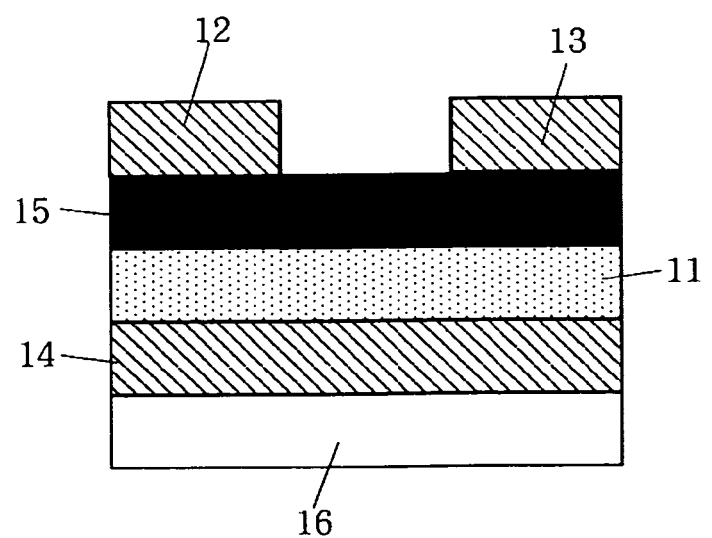
FIG. 2 is a cross-sectional view illustrating another embodiment of the configuration of the organic thin-film transistor according to the present invention.

A description will next be made about the configuration of the organic thin-film transistor according to the present invention. FIGS. 1 and 2 are cross-sectional views illustrating different embodiments of the configuration of the organic thin-film transistor according to the present invention, respectively. In the configuration of the organic thin-film transistor as illustrated in FIG. 1, a gate electrode 14 is arranged on a substrate 16, an insulating layer 11 is stacked on the gate electrode, a source electrode 12 and a drain electrode 13 are formed with a predetermined interval therebetween on the insulating layer 11, and further, an organic semiconductor layer 15 is stacked on the insulating layer 11, source electrode 12 and drain electrode 13 to form a bottom-gate, bottom-contact configuration. In the configuration of the organic thin-film transistor as illustrated in FIG. 2, a gate electrode 14 is arranged on a substrate 16, an insulating layer 11 is stacked on the gate electrode, an organic semiconductor layer 15 is stacked on the insulating layer 11, and further, a source electrode 12 and a drain electrode 13 are stacked with a predetermined interval therebetween on the organic semiconductor layer 15 to form a bottom-gate, top-contact configuration.

The transistor device having one of such configurations performs a switching operation when a voltage is applied between the gate electrode and the source electrode and by the voltage so applied, an organic semiconductor layer forms a channel region to control an electric current that flows between the source electrode and the drain electrode.

To form the organic semiconductor thin film with the organic semiconductor material according to the present invention, the use of a solution process is preferred although a vacuum deposition process, a sputtering process or the like is also usable. According to the solution process, the organic semiconductor material is dissolved in a solvent, and the resulting solution is applied to form an organic semiconductor thin film. Therefore, the solution process can realize further simplification of fabrication facilities and a further reduction in fabrication cost, and can also form an organic semiconductor thin film with a large area. Also preferred is to use a solution process that forms an organic semiconductor thin film by applying a dispersion of the organic semiconductor material in a solvent or water. For example, an organic semiconductor thin film can be formed by a process such as, for example, spin coating, inkjet printing, screen printing, planographic printing, letterpress printing, or intaglio printing. It is to be noted that, when an organic semiconductor thin film is formed on a substrate by vacuum deposition, sputtering or solution deposition, the formation can be conducted with or without heating the substrate.

No particular limitation is imposed on the solvent for use in the solution process that forms the organic semiconductor thin film according to the present invention, insofar as a solution of adequate concentration can be obtained. Examples include halogenated hydrocarbon solvents such as chloroform, dichloroethane, chlorobenzene, dichlorobenzene, trichlorobenzene and chloronaphthalene; ketone solvents such as acetone, methyl ethyl ketone and methyl isobutyl ketone; ester solvents such as ethyl acetate and butyl acetate; ether solvents such as diethyl ether, dioxane and tetrahydrofuran; aromatic hydrocarbon solvents such as toluene, xylene and ethylbenzene; and aprotonic polar solvents such as tetrahydrofuran, sulfolane, N,N-dimethylformamide, N-methyl-2-pyrrolidone and dimethylsulfoxide. These solvents may be used either singly or in combination.

A description will next be made about the substrate that forms the organic thin-film transistor according to the present invention. As the substrate, a material having insulating properties is preferred. Examples include substrates of inorganic materials such as glass and alumina; and substrates of plastics such as polyimides, polyesters, polyethylene, polystyrene, polypropylene and polycarbonates. The use of a plastic substrate makes it possible to fabricate a lightweight, flexible organic thin-film transistor of excellent impact resistance. These substrates may be used either singly or in combination. It is to be noted that, when an electrically-conductive substrate, for example, a silicon substrate is used with an insulating layer such as a silicon oxide film formed on a surface of the silicon substrate, the substrate can also serve as a gate electrode.

A description will next be made about the gate insulating layer that forms the organic thin-film transistor according to the present invention. Examples of a material that forms the gate insulating layer include, but are not specifically limited to, inorganic materials such as $SiO_2$, $ZrO_2$, $Ta_2O_5$, $La_2O_3$, $Al_2O_3$ and $HfO_2$. As polymer-based insulating film materials, on the other hand, organic materials such as polyimides, polymethyl methacrylate, polyvinyl alcohol, polyvinyl chloride, polyacrylonitrile, polyvinylidene fluoride, polyethylene terephthalate, polyethersulfone and polycarbonates can be used. These insulating materials for the gate insulating layer may be used either singly or in combination.

No particular limitation is imposed on a process for forming such a gate insulating layer. Illustrative are dry processes such as vacuum deposition, CVD, sputtering and atmospheric-pressure plasma processing; and wet processes such as coating processes such as spray coating, spin coating, blade coating, dip coating, casting, roll coating, bar coating, die coating, air knife coating, slide hopper coating and extrusion, various printing processes, and inkjet printing. Depending on the properties of materials to be used, a desired process can be selected and applied. For example, $SiO_2$ may be formed as a layer on a silicon substrate by thermal oxidation, steam oxidation or plasma oxidation.

A gate insulating layer may be hydrophobized by chemical surface treatment to improve the compatibility between the gate insulating layer and an organic semiconductor layer, so that the organic semiconductor thin film can be uniformly formed to reduce a leak current. Although not specifically limited, such a hydrophobizing layer can be formed by solution coating or vacuum deposition of a silane coupling agent such as, for example, OTS (octadecyltrichlorosilane), ODS (octadecyltrimethoxysilane) or HMDS (hexamethyldisilazane) on the gate insulating layer.

A description will next be made about electrode materials for forming the organic thin-film transistor according to the present invention. As electrode materials for the source electrode, drain electrode and gate electrode, materials having electrical conductivity are used. Usable examples include metal materials such as gold, silver, copper, platinum, aluminum, lithium, sodium, potassium, magnesium, calcium, titanium, indium, palladium, manganese, molybdenum, barium, chromium, tungsten, tantalum, nickel, cobalt, iron, lead and tin, and alloys of these metal materials; electrically-conductive oxides such as $InO_2$, $ZnO_2$, $SnO_2$, ITO and IZO; carbon materials such as carbon black, fullerene, carbon nanotube and graphite; and electrically-conductive high-molecular compounds. More preferred are gold, aluminum, magnesium, calcium, ITO, IZO and gold/chromium alloy as they each have small electric resistance at the surface of contact with the organic semiconductor layer.

No particular limitation is imposed on a process for the formation of these electrodes. For example, they can be formed by using a process such as a printing process making use of a dispersion of an electrically-conductive material in a solution, a printing process making use of a solution of an electrically-conductive material in a solution, a vapor deposition process, or a sputtering process.

The source electrode and the drain electrode are arranged opposite each other. The inter-electrode distance (channel length) is one of parameters that determine transistor characteristics. An inter-electrode distance (channel length) not greater than 100 μm is generally usable without problem, with 50 μm or smaller being preferred. As the width of a region between the source electrode and the drain electrode (channel width), any width can be used without any particular limitation. The channel width may be preferably 10 mm or smaller, more preferably 6 mm or smaller, still more preferably 1 mm or smaller. However, a still longer channel width may be formed when the electrodes are each formed, for example, in a comb-shaped structure. The source electrode and drain electrode so formed can be used without problem insofar as they have a thickness in a range of from several nanometers to several hundreds micrometers. Preferably, however, the thicknesses of the source electrode and drain electrode may range from 30 nm to 30 Ξm.

The organic thin-layer transistor according to the present invention contains at least one layer of the compound of the present invention represented the formula (F) as an organic semiconductor layer. As the compound of the present invention represented by the formula (F), compounds represented by the formula (F) may be used either singly or in combination. The compound of the present invention represented by the formula (F) may also be used in combination with one or more of perylene and its derivatives and naphthalene diimide and its derivatives, although the content of the organic semiconductor material according to the present invention should preferably account for 90 wt % or higher.

The organic thin-film transistor according to the present invention may be provided on the entire part or a part of its outer circumferential surface with a gas barrier layer to reduce the effects of oxygen, water and the like in the atmosphere. Examples of a material that forms such a gas barrier layer include polyvinyl alcohol, ethylene-vinyl alcohol copolymer, polyvinyl chloride, and polyvinylidene chloride.

The organic thin-film transistor according to the present invention can be evaluated for transistor characteristics by electron mobility ($cm^2/Vs$), on/off ratio and threshold voltage (V). To obtain a large current in the organic thin-film transistor, it is particularly important that its electron mobility has a large value. The electron mobility may desirably be 0.001 $cm^2/Vs$ or higher. When organic thin-film transistors have an electron mobility of 0.001 $cm^2/Vs$, they can be used as memory cells or drive elements for electron paper displays. When organic thin-film transistors have an electron mobility of 0.01 $cm^2/Vs$ or higher, they can be used, for example, as drive elements for active matrices as replacements for amorphous silicon transistors. Further, for thin-film transistors to be used as drive elements, a high on/off ratio is needed to achieve a high contrast. This on/off ratio may be preferably from $10^3$ to $10^{15}$, more preferably from $10^4$ to $10^{10}$, still more preferably from $1.6 \times 10^4$ to $2.2 \times 10^8$.

EXAMPLES

Examples of the present invention will hereinafter be described.

Synthesis of Compound A

Synthesis of 2,5-[1,4-bis(N,N'-octyldiphthalimido)]-2,2'-bithiophene (Which has a Structure of the Above-Described Formula (III) and May Hereinafter be Called "DPIBT")

4-bromo-n-octylphthalimide and 5,5'-bis(4,4,5,5-tetramethyl-1,3,2-dioxaboran-2-yl)-2,2'-bithiophene were coupled together in the presence of a palladium catalyst by the Suzuki-Miyaura coupling reaction to synthesize the title compound. The resulting crude product was subjected to preparative isolation by column chromatography, and was then purified by recrystallization. After the purification, the yield of the title compound was 83%.

M.S. (EI): Calculated for $C_{40}H_{44}N_2O_4S_2$: 680.92. Found: 682.

Decomposition temperature: 437° C.
Glass transition point: 103° C.
Melting point: 224° C.

Synthesis of Compound B

Synthesis of 2,5-[1,4(N,N'-octyldiphthalimido)]-benzene (Which has a Structure of the Above-Described Formula (I) and May Hereinafter be Called "DPIBen")

4-Bromo-N-octylphthalimide and 1,4-bis(4,4,5,5-tetramethyl-1,3,2-dioxaboran-2-yl)-benzene were coupled together in the presence of a palladium catalyst by the Suzuki-Miyaura coupling reaction to synthesize the title compound. The resulting crude product was subjected to preparative isolation by column chromatography, and was then purified by recrystallization. After the purification, the yield of the title compound was 53%.

M.S. (EI): Calculated for $C_{38}H_{44}N_2O_4$: 592.79. Found: 593.

Decomposition temperature: 320° C.
Melting point: 182° C.

Synthesis of Compound C

Synthesis of 2,5-[1,4-bis(N,N'-octyldiphthalimido)]-cyanobenzene (Which has a Structure of the Above-Described Formula (II) and May Hereinafter be Called "DPITN")

4-(4,4,5,5-Tetramethyl-1,3,2-dioxaboran-2-yl)-N-octylphthalimide and 1,4-dichloro-2,5-dicyanobenzene were coupled together in the presence of a palladium catalyst by the Suzuki-Miyaura coupling reaction to synthesize the title compound. The resulting crude product was subjected to preparative isolation by column chromatography, and was then purified by recrystallization. After the purification, the yield of the title compound was 33%.

M.S. (EI): Calculated for $C_{40}H_{42}N_2O_4$: 642.81. Found: 643.

Decomposition temperature: 420° C.
Melting point: 286° C.

Synthesis of Compound D

Synthesis of 2,5-[1,4-bis(N,N'-octyldiphthalimido)]-thienothiophene (Which has a Structure of the Above-Described Formula (IV) and May Hereinafter be Called "DPITT")

4-(4,4,5,5-Tetramethyl-1,3,2-dioxaboran-2-yl)-N-octylphthalimide and 2,5-dibromothieno(3,2-b)thiophene were coupled together in the presence of a palladium catalyst by the Suzuki-Miyaura coupling reaction to synthesize the title compound. The resulting crude product was subjected to preparative isolation by column chromatography, and was then purified by recrystallization. After the purification, the yield of the title compound was 56%.

M.S. (EI): Calculated for $C_{40}H_{42}N_2O_4S_2$: 654.89. Found: 655.

Synthesis of Compound E

Synthesis of 2,6-[1,4-bis(N,N'-octyldiphthalimido)]-anthracene (Which has a Structure of the Above-Described Formula (V) and May Hereinafter be Called "DPIAn")

4-(4,4,5,5-Tetramethyl-1,3,2-dioxaboran-2-yl)-N-octylphthalimide and 2,6-dibromoanthracene were coupled together in the presence of a palladium catalyst by the Suzuki-Miyaura coupling reaction to synthesize the title compound. The resulting crude product was subjected to preparative isolation by column chromatography, and was then purified by recrystallization. After the purification, the yield of the title compound was 56%.

M.S. (EI): Calculated for $C_{46}H_{48}N_2O_4$: 692.89. Found: 693.

Example 1

Fabrication of Organic Thin-Film Transistor with Compound A (DPIBT)

A silicon substrate, which had on a surface thereof a silicon oxide film (thickness: 300 nm) to be used as a gate insulating layer, was provided as a gate electrode and the gate insulating layer. The silicon substrate was immersed for 8 hours in a 1.0 wt % solution of HMDS in toluene to form an HMDS-SAM layer (hexamethylene disilazane-self-assembled monolayer) on a surface of the silicon oxide film. An organic semiconductor thin film (thickness: 50 nm) composed of DPIBT was formed on the HMDS-SAM layer by a vacuum deposition process (deposition rate: 0.05 [nm/sec]). Through a shadow mask, a pattern of gold electrodes (30 nm) was then formed as source/drain electrodes to fabricate a top-contact organic thin-film transistor. At that time, the channel length and channel width were set at 50 μm and 5,500 μm, respectively. Characteristics of the field-effect transistor fabricated as described above were evaluated.

Figure 3:
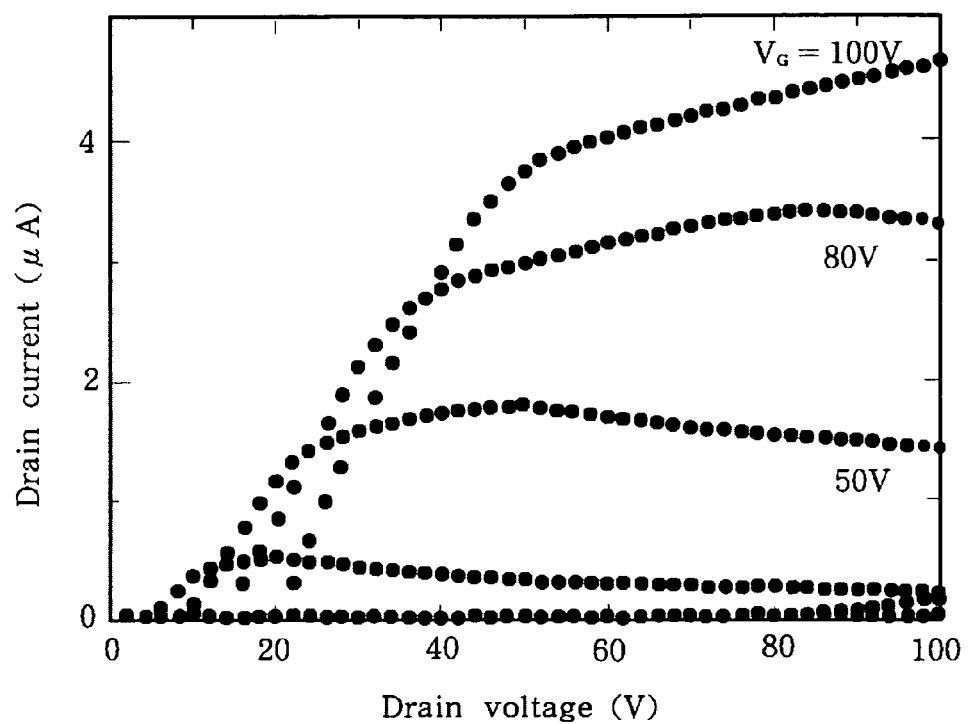
FIG. 3 is a diagram showing measurement values of drain voltage and drain current at different gate voltages.

With respect to the transistor, the drain voltage and drain current were measured at different gate voltages. The results are shown in FIG. 3. As is evident from FIG. 3, pronounced saturation regions were observed on the drain current-drain voltage curves, and therefore, it was demonstrated that this transistor is drivable as a field-effect transistor having typical n-type characteristics. The electron mobility, threshold voltage value and on/off ratio calculated from the curves were $4.7\times10^{-3}$ cm$^2$/Vs, 60 V and $4.9\times10^6$, respectively.

Example 2

Next, Compound B (DPIBen) was used in place of Compound A used in Example 1.

A silicon substrate, which had on a surface thereof a silicon oxide film (thickness: 300 nm) to be used as a gate insulating layer, was provided as a gate electrode and the gate insulating layer. The silicon substrate was immersed for 8 hours in a 1.0 wt % solution of HMDS in toluene to form an HMDS-SAM layer on a surface of the silicon oxide film. An organic semiconductor thin film (thickness: 50 nm) composed of DPIBen was formed on the HMDS-SAM layer by a vacuum deposition process (deposition rate: 0.05 [nm/sec]; substrate temperature: 120° C.). Patterning of electrodes was conducted in a similar manner as in Example 1 to obtain an organic thin-film transistor of Example 2. With respect to the transistor, the drain voltage and drain current were measured at different gate voltages. Pronounced saturation regions were observed on drain current-drain voltage curves at the different gate voltages, and therefore, it was demonstrated that this transistor is drivable as a field-effect transistor having typical n-type characteristics. Values of transistor characteristics as calculated from the drain current-drain voltage curves are shown in Table 1.

Example 3

An organic thin-film transistor was next fabricated in a similar manner as in Example 2 except that Compound C (DPITN) was used in place of Compound B. With respect to the transistor, the drain voltage and drain current were measured at different gate voltages. Pronounced saturation regions were observed on drain current-drain voltage curves at the different gate voltages, and therefore, it was demonstrated that this transistor is drivable as a field-effect transistor having typical n-type characteristics. Values of transistor characteristics as calculated from the drain current-drain voltage curves are shown in Table 1.

Example 4

An organic thin-film transistor was next fabricated in a similar manner as in Example 2 except that Compound A (DPIBT) was used in place of Compound B. With respect to the transistor, the drain voltage and drain current were measured at different gate voltages. Pronounced saturation regions were observed on drain current-drain voltage curves at the different gate voltages, and therefore, it was demonstrated that this transistor is drivable as a field-effect transistor having typical n-type characteristics. Values of transistor characteristics as calculated from the drain current-drain voltage curves are shown in Table 1.

Example 5

The procedure of Example 1 was followed. A silicon substrate, which had on a surface thereof a silicon oxide film (thickness: 300 nm) to be used as a gate insulating layer, was provided as a gate electrode and the gate insulating layer. The silicon substrate was immersed for 8 hours in a 1.0 wt % solution of HMDS in toluene to form an HMDS-SAM layer on a surface of the silicon oxide film. Compound A (DPIBT) employed in Example 1 was dissolved in chloroform to give a concentration of 1 wt %, and by a spin coater, an organic semiconductor film was formed on an HMDS-SAM film formed on the silicon substrate while heating the silicon substrate at 120° C. Patterning of electrodes was conducted in a similar manner as in Example 1 to obtain an organic thin-film transistor of Example 5. With respect to the transistor, the drain voltage and drain current were measured at different gate voltages. Pronounced saturation regions were observed on drain current-drain voltage curves at the different gate voltages, and therefore, it was demonstrated that this transistor is drivable as a field-effect transistor having typical n-type characteristics. Values of transistor characteristics as calculated from the drain current-drain voltage curves are shown in Table 1.

Examples 6-10

Using Compound A (DPIBT), Compound B (DPIBen), Compound C (DPITN), Compound D (DPITT) and Compound E (DPIAn) and heated silicon substrates having HMDS-SAM films, respectively, organic thin-film transistors were obtained in a similar manner as in Example 1. It was demonstrated that these transistors are drivable as field-effect transistors having typical n-type characteristics. Values of transistor characteristics as calculated from drain current-drain voltage curves are shown in Table 2

TABLE 1

| | Organic semiconductor material | Electron mobility (cm$^2$/Vs) | On/off ratio | Threshold voltage (V) |
|---|---|---|---|---|
| Example 1 | DPIBT | $4.7 \times 10^{-3}$ | $4.9 \times 10^6$ | 60 |
| Example 2 | DPIBen | $4.8 \times 10^{-3}$ | $4.9 \times 10^4$ | 60 |
| Example 3 | DPITN | 0.01 | $1.2 \times 10^6$ | 46 |
| Example 4 | DPIBT | 0.57 | $1.6 \times 10^4$ | 46 |
| Example 5 | DPIBT | 0.036 | $6.7 \times 10^6$ | 33 |

TABLE 2

| | Organic semiconductor material | Substrate temperature (° C.) | Electron mobility (cm$^2$/Vs) | On/off ratio | Threshold voltage (V) |
|---|---|---|---|---|---|
| Example 6 | DPIBT | 120 | 0.025 | $5.4 \times 10^4$ | 50 |
| Example 7 | DPIBen | 100 | 0.021 | $4.0 \times 10^5$ | 43 |
| Example 8 | DPITN | 140 | 0.13 | $2.2 \times 10^8$ | 52 |
| Example 9 | DPITT | 100 | 0.063 | $6.1 \times 10^5$ | 41 |
| Example 10 | DPIAn | 120 | 0.016 | $1.0 \times 10^5$ | 30 |

The present invention has been described above based on the preferred examples. It should, however, be borne in mind that the present invention is by no means limited to the above-described examples.

INDUSTRIAL APPLICABILITY

According to the present invention, it is possible to provide an organic semiconductor material, which has high electron mobility and high on/off ratio and permits the formation of an organic semiconductor thin film by a solution process making use of its solution. It is also possible to provide an organic thin-film transistor which can be fabricated with the organic semiconductor material.

REFERENCE SIGNS LIST

11: Gate insulating layer
12: Source electrode
13: Drain electrode
14: Gate electrode
15: Organic semiconductor layer
16: Substrate

The invention claimed is:

1. An organic semiconductor material represented by the following formula (F):

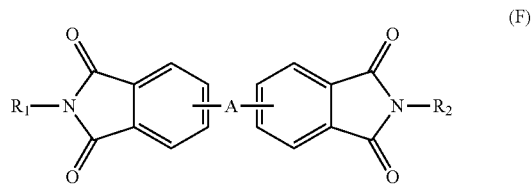

(F)

wherein A represents a substituted or unsubstituted benzene ring, naphthalene ring, anthracene ring, phenanthrolene ring, pyrene ring, triphenylene ring, naphthacene ring, pentacene ring, biphenyl ring, thiophene ring, bithiophene ring, terthiophene ring, quaterthiophene ring, quinquethiophene ring, sexithiophene ring, septithiophene ring, octithiophene ring, benzothiophene ring, thienothiophene ring, or dithienothiophene ring, and R$_1$ and R$_2$ each independently represent an alkyl group hydrogen atoms of which have been partly substituted by a like number of fluorine atoms or are unsubstituted.

2. The organic semiconductor material according to claim 1, wherein R$_1$ and R$_2$ each independently represent a linear or branched, C$_{1-18}$ alkyl group.

3. The organic semiconductor material according to claim 1, wherein R$_1$ and R$_2$ each independently represent a linear or branched, C$_{1-18}$ alkyl group hydrogen atoms of which have been partly substituted by a like number of fluorine atoms.

4. The organic semiconductor material according to claim 1, wherein A contains one or more fluorine atoms, bromine atoms, chlorine atoms or cyano groups as substituents.

5. The organic semiconductor material according to claim 1, wherein A comprises 1 to 4 aromatic rings.

6. The organic semiconductor material according to claim 1, wherein A has one of the following structures (1) to (7)

(1)

-continued

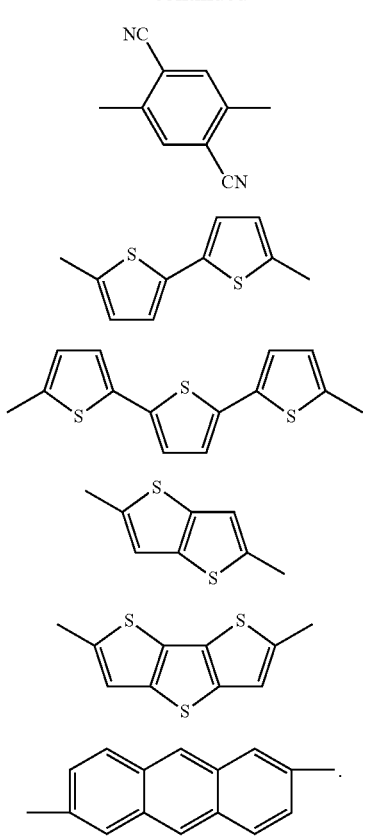

7. An organic semiconductor thin film comprising an organic semiconductor material according to claim 1.

8. An n-type organic thin-film transistor formed on a substrate and having a gate electrode, gate insulating layer, organic semiconductor layer, source electrode and drain electrode, wherein the organic semiconductor layer comprises an organic semiconductor thin film according to claim 7.

9. An n-type organic thin-film transistor according to claim 8, which has an electron mobility of from 0.001 to 5.0 cm$^2$/Vs.

10. An organic semiconductor thin film comprising an organic semiconductor material according to claim 2.

11. An n-type organic thin-film transistor formed on a substrate and having a gate electrode, gate insulating layer, organic semiconductor layer, source electrode and drain electrode, wherein the organic semiconductor layer comprises an organic semiconductor thin film according to claim 10.

12. An n-type organic thin-film transistor according to claim 11, which has an electron mobility of from 0.001 to 5.0 cm$^2$/Vs.

13. An organic semiconductor thin film comprising an organic semiconductor material according to claim 3.

14. An n-type organic thin-film transistor formed on a substrate and having a gate electrode, gate insulating layer, organic semiconductor layer, source electrode and drain electrode, wherein the organic semiconductor layer comprises an organic semiconductor thin film according to claim 13.

15. An n-type organic thin-film transistor according to claim 14, which has an electron mobility of from 0.001 to 5.0 cm$^2$/Vs.

16. An organic semiconductor thin film comprising an organic semiconductor material according to claim 4.

17. An n-type organic thin-film transistor formed on a substrate and having a gate electrode, gate insulating layer, organic semiconductor layer, source electrode and drain electrode, wherein the organic semiconductor layer comprises an organic semiconductor thin film according to claim 16.

18. An n-type organic thin-film transistor according to claim 17, which has an electron mobility of from 0.001 to 5.0 cm$^2$/Vs.

* * * * *